(12) United States Patent
Nho et al.

(10) Patent No.: US 7,799,352 B2
(45) Date of Patent: Sep. 21, 2010

(54) THERAPEUTIC HYDROGEL FOR ATOPIC DERMATITIS AND PREPARATION METHOD THEREOF

(75) Inventors: Young-Chang Nho, Seoul (KR); Youn-Mook Lim, Jeollabuk-do (KR); Sung-Jun An, Jeollabuk-do (KR); Yun-Hye Kim, Jeollanam-do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 11/832,944

(22) Filed: Aug. 2, 2007

(65) Prior Publication Data

US 2008/0038325 A1     Feb. 14, 2008

(30) Foreign Application Priority Data

Aug. 9, 2006  (KR) ................ 10-2006-0075156
Feb. 1, 2007  (KR) ................ 10-2007-0010605

(51) Int. Cl.
*A61K 36/00* (2006.01)
*A61K 36/53* (2006.01)
*A61K 36/534* (2006.01)
*A61K 36/28* (2006.01)
*A61K 36/20* (2006.01)

(52) U.S. Cl. ............... 424/725; 424/774; 424/747; 424/764; 424/769; 424/771

(58) Field of Classification Search ............... None
See application file for complete search history.

(56) References Cited

U.S. PATENT DOCUMENTS

| | | | |
|---|---|---|---|
| 5,389,376 A | 2/1995 | Duan et al. | |
| 5,480,717 A | 1/1996 | Kundel | |
| 2001/0053897 A1* | 12/2001 | Frate et al. | 604/304 |
| 2002/0009503 A1* | 1/2002 | Kotani et al. | 424/725 |
| 2002/0048603 A1* | 4/2002 | Burmeister et al. | 424/486 |
| 2004/0202706 A1* | 10/2004 | Koo et al. | 424/449 |
| 2005/0163878 A1* | 7/2005 | Kanda | 424/770 |
| 2006/0182770 A1* | 8/2006 | Tanojo et al. | 424/400 |
| 2006/0228416 A1* | 10/2006 | Faure et al. | 424/486 |

FOREIGN PATENT DOCUMENTS

| | | | |
|---|---|---|---|
| EP | 1025835 A2 * | 8/2000 | |
| JP | 9267453 | 10/1997 | |
| JP | 2002265327 A * | 9/2002 | |
| KR | 10-2001-0086864 | 9/2001 | |
| KR | 10-2003-0060458 | 7/2003 | |
| KR | 10-2004-0085646 | 10/2004 | |
| KR | 2005106194 A * | 11/2005 | |
| KR | 10-2006-0015842 | 2/2006 | |
| KR | 2006029807 A * | 4/2006 | |
| RU | 2107510 * | 3/1998 | |
| RU | 2107510 C1 * | 3/1998 | |

OTHER PUBLICATIONS

Cho et al., Study on the inhibitory effects of Korean medicinal plants and their main compounds on the 1,1-diphenyl-2-picrylhydrazyl radical, Phytomedicine: international journal of phytotherapy and phytopharmcology, (2003) 10 (6-7): 544-51.*
Sarkozi et al, Mineral element content of greater celandine (Chelidonium majus L., Acta Alimentaria (2005), 34 (2), 113-120.*
Definition of Celandine from Wikipedia, accessed on Jan. 17, 2010, pp. 1.*
Definition of persimmon, accessed on Jan. 17, 2010, pp. 1-9.*

* cited by examiner

*Primary Examiner*—Qiuwen Mi
(74) *Attorney, Agent, or Firm*—Lucas & Mercanti, LLP

(57) ABSTRACT

Disclosed are therapeutic hydrogels for atopic dermatitis and a method for preparing the same. The hydrogels comprises a biocompatible polymer, a polyalcohol, and a medicinal plant extract. The hydrogels can carry medicinally effective ingredients for a sustained period of time and absorb wound exudates properly. The hydrogels have suitable gel strength and, when applied to a wound, can prevent bacterial infection of the wound. Moreover, the methods employing radiation allow the polymer chains to be crosslinked to each other, and also bring about a sterilization effect in the final hydrogel. There are no problems of toxic residues in the hydrogels. They are easy to attach to the skin and concomitantly provide a cool feeling. Supported by the laminate of hydrophilic non-woven fabric sheet and polyethylene film, the hydrogel retain water for a prolonged period of time and thus are useful in the treatment of contact dermatitis and atopic dermatitis.

17 Claims, 12 Drawing Sheets

Sterile package

Package open

Gel surface

Supported by
Water evaporation
preventive membrane (a) DNFB (0.5%)

(b) DNFB (0.5%)

compound 48/80 injection before after before after before after before after

THERAPEUTIC HYDROGEL FOR ATOPIC DERMATITIS AND PREPARATION METHOD THEREOF

BACKGROUND OF THE INVENTION

1. Field of the Invention

The present invention relates to hydrogels effective for the treatment of atopic dermatitis, comprising biocompatible polymers, polyalcohols, and extracts from medicinal herbs.

2. Description of the Related Art

Atopy is an allergic hypersensitivity that predisposes a person to certain allergic responses, such as atopic dermatitis. Atopic dermatitis is a chronic/inflammatory skin disease, which is the hereditary predisposition to allergies or hypersensitivity. It is a familial and chronic disease with characteristic forms and distributions of skin lesions. Atopic dermatitis is typically found in people having an atopic predisposition. Its symptoms start as congenital fever from infancy, especially in babies around two months after birth. About 50% of patients are reported to suffer from atopic dermatitis from two years after birth or earlier. Atopic dermatitis occurs, for the most part, 5 years after birth at the latest. A medical rarity is the start of atopic dermatitis in adults. Its symptoms are relieved or disappear over time. It is known that the condition of half of the patients changes for the better 2 years after birth or earlier.

Atopic dermatitis is largely typified by pruritus, xerosis (dry skin), and eczematous lesions. Scratching the itchy spots may result in skin damage which gives rise to an increase in the risk of bacterial infection. Xerosis aggravates pruritus, which causes the person to scratch. Scratching or rubbing the skin can make the itch and rash of atopic dermatitis worse. Therefore it is important to prevent the skin from drying out upon treatment for atopic dermatitis.

The exact pathological cause of atopic dermatitis remains unknown. It is believed that together with hereditary predisposition, immunological and non immunological mechanisms are implicated in atopic dermatitis. Extrinsic atopic dermatitis, from which most patients suffer, is caused by the presence of elevated levels of total and allergen-specific IgE in the serum of the patients. Primary immune responses based on T-cell abnormality as well as or rather than secondary immune responses to specific allergens are involved in the pathological mechanism of atopic dermatitis, as cell-mediated immunity in patients with atopic dermatitis is known to be related to the elevated level of IgE.

In up to about 80% of patients with atopic dermatitis, immune disorders are detected. Such patients tend to show hypersensitivity to cutaneous infection by viruses and dermatophytes and hyposensitivity to contagious allergens. In the past, deficiency in T-cell maturation and a decrease in the number of CD8+ regulatory T-cells were reported. However, it was recently observed that CD4+ T-cells play a more important role in the mechanism of atopic dermatitis. T-cells which secrete IL-4 and IL-5, inducers or promoters for the production of IgE from B cells, and IL-6, an amplifier for the production of IgE from B cells, are Th2 cells, among CD4+ T-cells. It is found that the level of Th2 cells is higher than that of Th1 cells in the skin of atopic dermatitis patients. These cytokines are known to stimulate mast cells, macrophages and basophils to induce the secretion of histamine, leukotriene, prostaglandin and nitrogen monoxide (NO), which are inflammation mediators responsible for the inflammatory response of the skin.

In consideration of the pathology, mechanism and symptoms known thus far, extensive attempts have been made to develop therapeutics for atopic dermatitis. As a result, natural or synthetic immunosuppressants, steroids, and anti-histamine agents are currently commercialized. Conventional steroid agents and anti-histamine agents for the treatment of atopic dermatitis relieve the symptoms of atopic dermatitis temporarily, but not permanently.

Reversing xerosis is one of the key elements in the treatment of atopic dermatitis. Using emollients is considered standard therapy in treating patients with AD. However, conventional emollients, for example, moisturizers containing beeswax, glycerin, propylene glycol, and fatty acids, do not show excellent moisturizing effects due to their inability to effectively regulate moisture evaporation.

One of the uses for hydrogels is as a dressing for healing of burns or for dermal regeneration of wounds. For use for this purpose, hydrogels must have a water content of at least 60%. Also, being biocompatible with blood, humoral fluid and bio-tissues, these hydrogels can be applied to contact lenses and cartilage.

The preparation of such hydrogels applicable for these uses is based on a polymer which can be formed into hydrogel. Typically, hydrogel has a three-dimensional network structure of polymer chains containing hydrophilic functional groups such as carboxylic group (—COOH), amide group (—$CONH_2$), and sulfonyl group (—$SO_3H$), and is water-insoluble, but swells in aqueous solution. In greater detail, hydrogels, which have an insoluble network of polymer chains, absorb water thanks to their characteristic structures accounting for capillary and osmotic phenomena, but are insoluble in water due partly to their electrostatic and lipophilic interaction between polymer chains and mainly to covalent bonds between polymer chains.

Typically, hydrogels are prepared from synthetic polymers, naturally occurring polymers or combinations thereof. Examples of the synthetic polymers include hydrophilic synthetic polymers such as polyvinyl alcohol, polyethylene oxide, polyhydroxyethylmethacrylate, polyvinylpyrrolidone, and so on, but are limited thereto Naturally occurring polymers useful in the preparation of hydrogels may be found among carrageenan, gelatin, agar, alginate, collagen and chitosan.

The preparation of hydrogels may resort to chemical methods or radiation methods. Keen attention is paid to radiation methods because they have the advantage over chemical methods in various aspects. First, because radiation methods employ neither crosslinking agents nor initiators for the crosslinking of polymer chains, in contrast to chemical methods, there is no need to remove crosslinking agents and initiators out of fear of toxicity. Radiation can give rise to both crosslinking and sterilization. Also, radiation methods, which require no heat, make it possible to crosslink polymers even in a frozen state. Even the physical properties of the final product hydrogels can be freely adjusted with a radiation dose.

Various methods for preparing hydrogels are documented in the literature. U.S. Pat. No. 5,389,376 discloses a method of preparing hydrogel dressings for wound healing through radiation crosslinking. In this method, polyvinylpyrrolidone is mixed with agar and polyethylene oxide, followed by radiation to crosslink the polymers. Of course, this method enjoys the advantage of the radiation method, that is, effecting both crosslinking and sterilizing simultaneously, but polyvinylidone and agar are poorly miscible, resulting in a reduction in the strength of the final product hydrogels.

U.S. Pat. No. 5,480,717 discloses processes in which a hydrogel laminate is formed by casting onto a polymeric adhesive-coated substrate an aqueous solution of hydrophilic polymer, and then exposing this composite to ionizing radiation. The hydrogel laminate is weak in hydrogel strength, but its excessively strong adhesiveness causes polyvinylidone to remain on the wound when the laminate is detached therefrom.

Japanese Patent Laid-Open Publication No. Hei. 9-267453 describes a laminate based on a polyvinyl alcohol substrate having improved physical properties. However, the simple radiation of this patent cannot bring about a great improvement in the physical properties of the laminate. In addition, two rounds of radiation are required, because the laminate cannot be packed while maintaining the integrity of the form unless radiation is conducted.

Korean Patent Laid-Open Publication No. 2001-0086864 discloses a method of preparing hydrogel dressings for wound healing, comprising: mixing a synthetic polyvinylidone polymer with chitosan, chitosan and polyethylene oxide, or sodium alginate and polyethylene oxide to give an aqueous solution (step 1); molding the aqueous solution of step 1 into a sheet form (step 2); packaging the sheet of step 2 (step 3); and radiating the packaged sheet of step 3 (step 4). Another method of preparing a hydrogel for wound healing is disclosed in Korean Patent Laid-Open Publication No. 2003-0060458, which comprises coating on a membrane either an aqueous solution of a biocompatible polymer selected from among polyvinylidone, polyvinyl alcohol, chitosan and combinations thereof, or an aqueous solution of a mixture of the biocompatible polymer and glycerin, freezing and thawing the coating to form a pre-hydrogel; packaging the pre-hydrogel molded on the membrane with a sheet; and radiating the packaged pre-hydrogel. Korean Patent Laid-Open Publication No. 2004-0085646 suggested a hydrogel dressing prepared from a composition comprising polyvinylidone, polyalcohol and carrageenan, a preparation method thereof using a tray and radiation, and a dressing for wound healing and a cosmetic skin pack using the same.

The available time of these hydrogels is too short. When exposed to air for 12 hours, these hydrogels, however, evaporate and thus cannot function as therapeutics for wounds.

A solution to these problems was proposed in Korean Patent No. 61237, which discloses a hydrogel for wound healing, prepared by coating an aqueous solution of a biocompatible polymer selected from among polyvinylidone, polyethyleneglycol, carrageenan and combinations thereof on an ethylene vinylacetate(EVA) copolymer film, an ethylene vinylalcohol(EVOH) copolymer, a very low density polyethylene(LDPE) film or a polyurethane membrane to form a pre-hydrogel, and crosslinking the biocompatible polymer with radiation to give a hydrogel containing a water evaporation-preventive layer.

This hydrogel can prolong the release of water for about 60 hours, but the lack of air permeability of the film employed in the hydrogel makes it impossible to apply the hydrogel to the treatment of atopic dermatitis.

Leading to the present invention, intensive and thorough research into hydrogels usefully applicable for the treatment of dermatitis, conducted by the present inventors, resulted in the finding that an extract from medicinal plants which is effective in the treatment of dermatitis, especially contact dermatitis and atopic dermatitis, can be released for a suspended period of time when it is associated with a network structure of polymer chains, and that, when supported by a laminate of a hydrophilic non-woven fabric sheet and an air-permeable polyethylene film, the hydrogel can retain water for a suspended period of time, thereby allowing the skin to be kept wet during the application thereof to the skin. Therefore, the hydrogel significantly relieves pruritus and prevents secondary wounds attributed to scratching.

SUMMARY OF THE INVENTION

Accordingly, the present invention has been made keeping in mind the above problems occurring in the prior art, and an object of the present invention is to provide a hydrogel for the treatment of atopic dermatitis.

In order to accomplish the above object, the present invention provides a hydrogel for the treatment of contact dermatitis or atopic dermatitis, comprising a biocompatible polymer, a polyalcohol and a medicinal plant extract.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Figure 1:
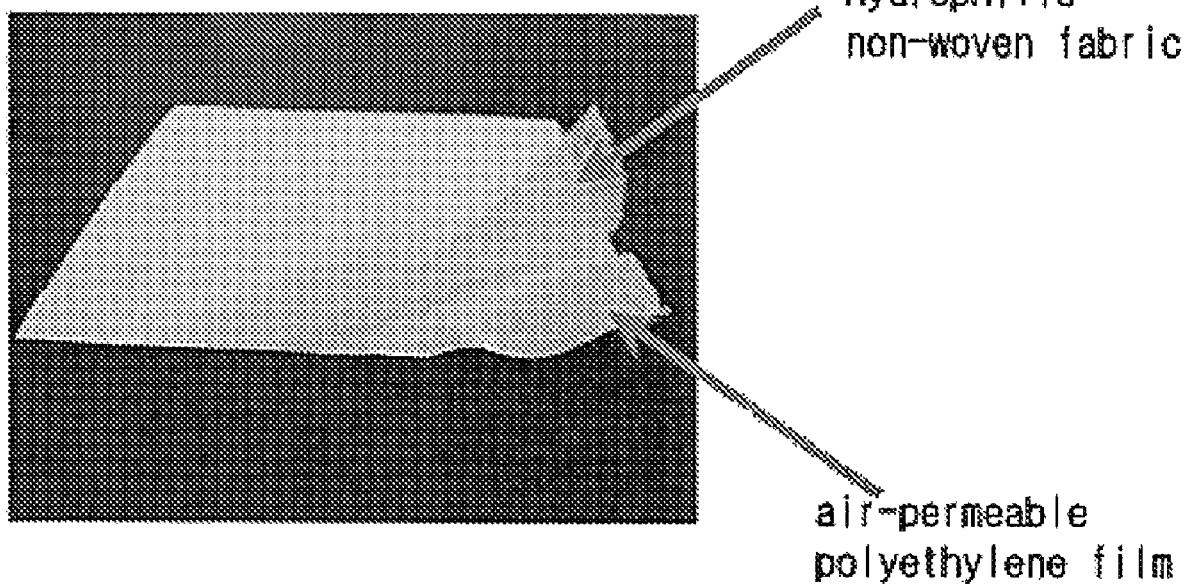
FIG. 1 is a photograph showing a laminate functioning as a water evaporation preventive membrane in a hydrogel for the treatment of atopic dermatitis in accordance with an embodiment of the present invention.

With reference to the accompanying drawings, a detailed description will be given of the present invention below.

The present invention provides a hydrogel for the treatment of atopic dermatitis, comprising a biocompatible polymer, a polyalcohol, and a medicinal herb extract.

In a preferable embodiment of the present invention, the hydrogel comprises the biocompatible polymer in an amount of 1~50 wt %, the polyalcohol in an amount of 1~20 wt %, and the medicinal herb extract in an amount of 1~30 wt %.

For use in the hydrogel according to the present invention, the biocompatible polymer is insoluble in water but swells therein because it has a three dimensional network structure and a hydrophilic functional group. In accordance with an embodiment of the present invention, the biocompatible polymer useful in the preparation of the hydrogel may be a synthetic polymer selected from a group consisting of polyvinyl alcohol, polyvinylpyrrolidone, polyacrylic acid, and polyethylene oxide, a natural polymer selected from a group consisting of carrageenan, sodium carboxymethyl cellulose, gelatin, agar, alginate and chitosan, or a combination of the synthetic polymer and the natural polymer. Preferably, polyvinyl alcohol alone may be used as the biocompatible polymer. In another preferable embodiment, polyvinylpyrrolidone or polyacrylic acid is used in combination with carrageenan as the biocompatible polymer. In terms of strength, the hydrogel preferably comprises polyvinyl alcohol in an amount of 1~50 wt %, polyvinylpyrrolidone in an amount of 1~30 wt %, polyacrylic acid in an amount of 1~20 wt %, or carrageenan in an amount of 1~5 wt %.

Polyvinyl alcohol, a hydrophilic polymer suitable as a biomaterial, has excellent mechanical and thermal strength and can be crosslinked physically, for example, through several rounds of freezing and thawing. Having these physical properties, polyvinyl alcohol is widely used for the preparation of various hydrogels and membranes.

Polyvinylpyrrolidone is widely used as a biomaterial thanks to the high water solubility and biocompatibility thereof. In addition, the oxygen and nitrogen atoms present within the structural unit of polyvinylpyrrolidone form hydrogen bonds with water molecules, resulting in a network structure, and allow the polymer to retain a great amount of water. Thus, this polymer is useful in the treatment of atopic dermatitis.

Carrageenan, a non-toxic, naturally occurring polymer, shows emollient and soothing effects on the skin and prevents the redness of the skin.

The other biopolymers can be formed into three-dimensional network structures having a high water retention capacity.

The polyalcohol functions to confer the hydrogel with adhesiveness and flexibility. For use in the hydrogel according to the present invention, however, the polyalcohol is required to be non-toxic to the body. The polyalcohol useful in the present invention is selected from a group consisting of glycerin, ethyleneglycol, propyleneglycol, 1-3-butyleneglycol, hexylene glycol, sorbitol, mannitol, polyethyleneglycol and combinations thereof with glycerin being preferred.

As long as it is effective in the treatment of atopic dermatitis, any medicinal plant extract may be used in the hydrogel according to the present invention. Preferable is an extract from a plant selected from a group consisting of *Houttuynia cordata*, elm, persimmon leaves, celandine, pine tree leaves, *Canavalia gladiata* and combinations thereof, optionally in combination with an extract from a herb selected form a group consisting of rosemary, lavender, spearmint, chamomile, rooibos and mixtures thereof.

Preferably, the medicinal plant extract is obtained from a plant mixture comprising 5~25 wt % of *Houttuynia cordata*, 5~25 wt % of elm, 5~25 wt % of persimmon leaves, 5~25 wt % of celandine, 5~25 wt % of pine tree leaves, 5~10 wt % of *Canavalia gladiata*, and 5~30 wt % of an herb. The medicinal plant extract can be prepared according to a method well known in the art.

The medicinal plants and herbs, whether nurtured or commercially available, can be used without limitation as long as they are clean. After being dried, the medicinal plants and herbs are chopped into suitable sizes and immersed in a suitable amount of distilled water or an organic solvent in a vessel. Extraction is performed at a predetermined temperature for 24~36 hours, followed by filtration through a filter to afford a medicinal plant extract.

Deionized water is preferably used as the distilled water. As for the organic solvent, it is preferably ethanol.

For the extraction, the temperature is preferably set in a range from 80 to 100° C. for distilled water and in a range from 50 to 70° C. for an organic solvent.

When the extraction is performed using an organic solvent, the filtrate obtained by filtering off the solid residue is evaporated in a vacuum evaporator to remove the organic solvent therefrom.

The medicinal plants, which are difficult to dry, can also be extracted in the same manner as for dried medicinal plants, with the exception that juice is squeezed from the wet plants and added to the distilled water.

Consisting of natural ingredients, the extract prepared in the method does not irritate the body, and is effective in the treatment of atopic dermatitis.

Optionally, the hydrogel according to the present invention further comprises a moisture-evaporation preventive layer.

In the hydrogel according to the present invention, the moisture-evaporation preventive layer is preferably composed of a laminate of a hydrophilic non-woven fabric and an air-permeable polyethylene film, as shown in FIG. 1.

While the hydrophilic non-woven fabric functions to confer strength to the hydrogel, the air-permeable polyethylene film is impermeable to moisture and thus prevents the evaporation of water and holds water within the hydrogel for a long period of time. Also, the air-permeable polyethylene film allows the skin to breathe.

The laminate of a hydrophilic non-woven fabric sheet and an air-permeable polyethylene film is a commercially available one, or may be prepared through a conventional process as long as it meets the above-mentioned requirements.

In accordance with another aspect thereof, the present invention provides a method of preparing the therapeutic hydrogel for atopic dermatitis, comprising:

casting a solution of a biocompatible polymer and a polyalcohol in a medicinal plant extract to form a gel (Step A);

freezing and thawing the cast gel (Step B); and crosslinking and sterilizing the thawed gel through radiation (Step C).

In Step A, the biocompatible polymer and the polyalcohol are dissolved in the medicinal plant extract and the solution is cast.

In order to confer proper strength on the final hydrogel, the biocompatible polymer is preferably used in an amount of 1~50 wt % on the basis of the weight of the total solution. For example, a content of the biocompatible polymer of less than 1 wt % cannot guarantee gel strength sufficient to support medicinally effective ingredients. On the other hand, when the content of the biocompatible polymer exceeds 50 wt %, the resulting aqueous solution is difficult to manage.

A preferable content of the polyalcohol falls into a range from 1 to 20 wt % based on the weight of the total aqueous solution. For example, when the content of the polyalcohol is less than 1 wt %, the resulting hydrogel has insufficient adhesiveness and flexibility. On the other hand, hydrogel having a polyalcohol content exceeding 20 wt % is too weak to accommodate the medicinally effective ingredients.

In Step B, the gel molded in Step A is frozen and thawed.

Through this freezing and thawing process, physically crosslinked bonds can be introduced into the cast gel. In this regard, it is important to form a hydrogel layer to a proper thickness, preferably to a thickness of 1~5 mm. For effective physical crosslinking, the freezing is preferably conducted at a temperature of $-100 \sim -15°$ C., and more preferably at a temperature of $-70 \sim -40°$ C. For the same purpose, the thawing temperature is preferably within a range from 5 to 50° C., and more preferably from 20 to 30° C.

Freezing at a temperature lower than $-100°$ C. makes an insignificant difference in the physical crosslinking of the gel. On the other hand, the gel is not frozen at a temperature higher than $-15°$ C. In addition, a temperature lower than 5° C. cannot secure a proper time period necessary for thawing, while the physically crosslinked bonds may be weakened at a thawing temperature higher than 50° C.

Although it is dependent on the temperature for freezing, the time for the freezing process is within a range from 5 min to 1 hour. When the freezing process is conducted for a period less than 5 min, the gel is not frozen effectively. On the other hand, a time period exceeding 1 hour is needlessly long.

The freezing and thawing process may be repeated in order to better the physically crosslinked bonds. Repetition may be conducted preferably from one to ten times, and more preferably from one to three times, in terms of process simplification.

In Step C, the thawed gel of Step B is crosslinked and sterilized by radiation.

Over chemical crosslinking methods, the irradiation method has an advantage in that it does not leave toxic materials in the hydrogel. In addition, irradiation simultaneously achieves crosslinking and sterilization. Radiation useful for crosslinking may be gamma radiation, UV radiation or electron beam radiation.

The radiation is preferably radiated at a dose of 2~200 kGy, and more preferably at a dose of 5~100 kGy. A radiation dose less than 2 kGy cannot guarantee the effective formation of crosslinked bonds between the biocompatible polymers. On the other hand, when the gel is irradiated with a beam at a radiation dose higher than 200 kGy, too many crosslinked bonds are formed, resulting in a rigid hydrogel. Also, the polymer is degenerated when it is exposed to a high radiation dose.

According to another embodiment of the present invention, a therapeutic hydrogel for atopic dermatitis can be prepared without the freezing/thawing process (Step B). That is, the gel can be directly crosslinked by radiation.

The same radiation source and dose as in the above method may be employed.

In accordance with another embodiment, the present invention provides a hydrogel for the treatment of atopic dermatitis, comprising a hydrogel and a moisture-evaporation preventive laminate. The hydrogel according to the present invention is prepared through a method comprising:

dissolving a biocompatible polymer and a polyalcohol in a medicinal plant extract to give an aqueous solution (Step 1);

casting the aqueous solution of Step 1 on a laminate composed of a hydrophilic non-woven fabric sheet and an air-permeable polyethylene film, said laminate functioning as a moisture-evaporation preventive layer to afford a pre-hydrogel (Step 2);

packaging the pre-hydrogel (Step 3); and radiating the package gel (Step 4).

In Step 1, a biocompatible polymer and a polyalcohol are dissolved in a medicinal plant extract to yield an aqueous solution.

In order to guarantee proper strength of the final hydrogel, the biocompatible polymer is preferably used in an amount of 1~50 wt % based on the weight of the total solution. A content of the biocompatible polymer less than 1 wt % cannot guarantee sufficient gel strength to support the medicinally effective ingredients. On the other hand, when the content of the biocompatible polymer exceeds 50 wt %, the resulting aqueous solution is difficult to manage.

A preferable content of the polyalcohol falls into a range from 1 to 20 wt % on the basis of the weight of the total aqueous solution. For example, when the content of the polyalcohol is less than 1 wt %, the resulting hydrogel has insufficient adhesiveness and flexibility. On the other hand, hydrogel having a polyalcohol content exceeding 20 wt % is too weak to accommodate the medicinally effective ingredients.

In Step 2, the aqueous solution of Step 1 is cast on a laminate of a hydrophilic non-woven fabric sheet and an air-permeable polyethylene film to form a pre-hydrogel.

In greater detail, the aqueous solution of Step 1 is applied onto a laminate of a hydrophilic non-woven fabric sheet and an air-permeable polyethylene film, and the coating is cast in a tray, followed by solidifying at room temperature or freezing and thawing to give a pre-hydrogel.

Functioning as a water evaporation preventive layer, the laminate of hydrophilic non-woven sheet and air-permeable polyethylene film preferably ranges in thickness from 10 to 500 μm. The laminate may be a commercially available one or a typically prepared one (for example, a UPC product).

Through this freezing and thawing process, physically crosslinked bonds can be introduced into the cast gel. In this regard, it is important that the hydrogel layer be formed to a proper thickness, preferably to a thickness of 1~5 mm. For effective physical crosslinking, the freezing is preferably conducted at a temperature ranging from $-100 \sim -15°$ C. and more preferably at a temperature ranging from $-70 \sim -40°$ C. For the same purpose, the thawing temperature is preferably within a range from 5 to 50° C. and more preferably from 20 to 30° C.

Freezing at a temperature lower than $-100°$ C. does not make a significant difference to the physical crosslinking of the gel. On the other hand, the gel does not freeze at a temperature higher than $-15°$ C. In addition, a temperature lower than 5° C. cannot secure a proper time period necessary for thawing, while the physically crosslinked bonds may be weakened at a thawing temperature higher than 50° C.

Although it is dependent on the temperature for freezing, the time for the freezing process is within a range from 5 min to 1 hour. When the freezing process is conducted for a period less than 5 min, the gel is not frozen effectively. On the other hand, a time period exceeding 1 hour is excessively long.

The freezing and thawing process may be repeated in order to better the physically crosslinked bonds. Repetition is preferably conducted from one to ten times and more preferably from one to three times in terms of process simplification.

In Step 3, the pre-hydrogel of Step 2 is packaged.

For this, a typical packing sheet may be used. For example, a polymeric film, such as polyethylene, polypropylene, polyvinyl chloride, nylon, polyester, etc., or a laminate of a polymeric film and aluminum foil may be used.

In step 4, the packaged gel of Step 4 is crosslinked and sterilized by radiation.

This irradiation method has an advantage over chemical crosslinking methods in that it does not leave toxic materials in the hydrogel. In addition, such irradiation can simultaneously achieve crosslinking and sterilization. Radiation useful in the crosslinking may be a gamma ray, a UV ray or an electron beam.

The radiation is preferably irradiated at a dose of 2~200 kGy, and more preferably at a dose of 5~100 kGy. A radiation dose less than 2 kGy cannot guarantee the effective formation of crosslinked bonds between the biocompatible polymers. On the other hand, when the gel is irradiated with a beam in a radiation dose higher than 200 kGy, too many crosslinked bonds are formed, resulting in rigid hydrogel. Also, the polymer is degenerated when it is exposed to a high radiation dose.

Figure 2:
FIG. 2 provides photographs showing various states of a hydrogel for the treatment of atopic dermatitis comprising a hydrogel supported by a water evaporation preventive membrane in accordance with an embodiment of the present invention.
Figure 2:
Figure 2:
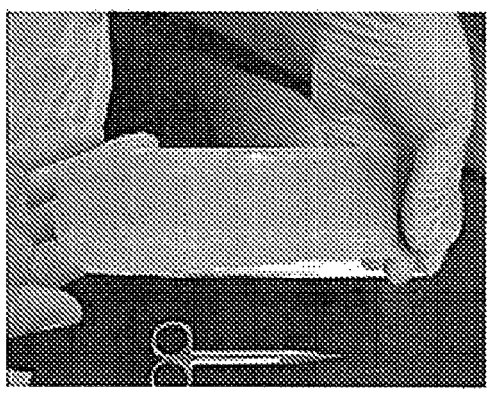
Figure 2:
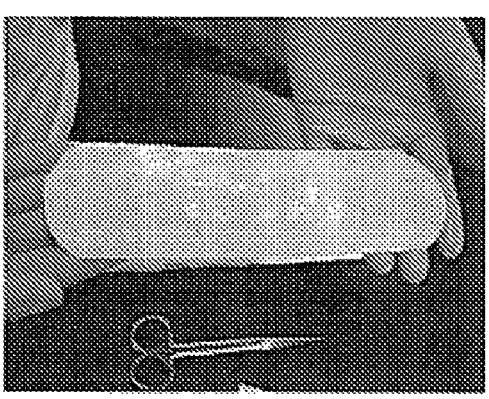

With reference to FIG. 2, a therapeutic hydrogel for atopic dermatitis, prepared according to the method of the present invention, is shown. As described above, the hydrogel can be prepared simply. Supported by the laminate of hydrophilic non-woven fabric sheet and water-impermeable, air-permeable polyethylene film, the hydrogel retains moisture for a long period of time and thus can achieve an excellent moisturization effect on the skin and release drugs for a sustained period of time. In addition, the hydrogel provides a cool feeling, is very strong, and protects the wound from being infected by bacteria. Further, irradiation crosslinks the polymer chains of the gel with the concomitant production of effects including increased preservability and sterilization. Also, the absence of any initiator and crosslinking agent means that there are no problems related to toxic residue, thus allowing the hydrogel to be applied to the skin safely. The hydrogel of the present invention is easy to handle. Consequently, the hydrogel according to the present invention can be effectively used for the treatment of contact dermatitis or atopic dermatitis.

A better understanding of the present invention may be obtained through the following examples which are set forth to illustrate, but are not to be construed as the limit of the present invention.

Preparation Example 1

Preparation of Medicinal Plant Extract 1

Dried *Houttuynia cordata*, elm, persimmon leaves, celandine, pine tree leaves, *Canavalia gladiata* and an herb (rosemary, lavender, spearmint, chamomile or rooibos) were immersed together in deionized water in an amount of 20 g each per 1 liter of water, followed by heating at 80° C. for 24 hours. Thereafter, the solid residues were filtered off from the solution to afford an extract.

Preparation Example 2

Preparation of Medicinal Plant Extract 2

The same plants and herbs as used in Preparation Example 1 were immersed in 70% ethanol(water:ethanol=30:70) at an amount of 20 g each per 1 liter of the ethanol, followed by heating at 60° C. for 24 hours. Thereafter, the solid residues were filtered off, and, using a vacuum evaporator, alcohol was removed from the resulting solution to afford an extract.

Preparation Example 3

Preparation of Medicinal Plant Extract 3

The same plants and herbs as used in Preparation Example 1 were immersed in deionized water in an amount of 20 g each per 1 liter of water, followed by autoclaving at 120° C. for 1 hour to afford an extract.

Preparation Example 4

Preparation of Extract from Medicinal Plant Mixture

Extracts were prepared in the same manner as in Preparation Examples 1 to 3, with the exception that 8 g of *Houttuynia cordata*, 8 g of elm, 2 g of persimmon leaves, 8 g of celandine, 10 g of pine tree leaves, 1 g of *Canavalia gladiata*, and 20 g of the herb were immersed in 1 liter of deionized water.

Example 1

Preparation of Polyvinyl Alcohol Hydrogel Through Freezing/Thawing Process 1

Polyvinyl alcohol and glycerin were dissolved in amounts of 20 wt % and 5 wt %, respectively, at 120° C. in the extracts prepared in Preparation Examples 1 to 4, and the resulting solutions were cast to a thickness of 1~3 mm. The cast was frozen at −76° C. for 5~10 min and then thawed at room temperature. The resulting gels were irradiated with Co-60 gamma ray in radiation doses of 25, 35, 50 and 75 kGy, respectively, to crosslink the polymer chains to afford sterile hydrogels.

Example 2

Preparation of Polyvinyl Alcohol Hydrogel Through Freezing/Thawing Process 2

The same procedure as in Example 1 was repeated, with the exception of using an electron beam accelerator instead of the gamma ray source, to afford hydrogels.

Example 3

Preparation of Polyvinyl Alcohol Hydrogel Through Freezing/Thawing Process 3

Hydrogels were prepared in the same manner as in Example 1, with the exception that a photoinitiator was added to the solution and a UV lamp (230~400 nm) was used instead of the gamma ray source.

Example 4

Preparation of Polyvinylpyrrolidone Hydrogel 1

Polyvinylpyrrolidone and carrageenan were dissolved in amounts of 7 wt % and 3 wt %, respectively, at 80° C. in the extracts (prepared in Preparation Examples 1 to 4), and the resulting solutions were cast to a thickness of 1~3 mm. The cast gels were irradiated with Co-Go gamma ray in radiation doses of 25, 35, 50 and 75 kGy, respectively, to crosslink the polymer chains to afford sterile hydrogels.

Example 5

Preparation of Polyvinylpyrrolidone Hydrogel 2

The same procedure as in Example 4 was repeated to afford hydrogels, with the exception that an electron beam accelerator was used instead of the gamma ray source.

Example 6

Preparation of Polyvinylpyrrolidone Hydrogel 3

Hydrogels were prepared in the same manner as in Example 4, with the exception that a photoinitiator was added to the solution and a UV lamp (230~400 nm) was used instead of the gamma ray source.

Example 7

Preparation of Polyacrylic Acid Hydrogel 1

Polyacrylic acid and carrageenan were dissolved in amounts of 10 wt % and 3 wt %, respectively, in the extracts (prepared in Preparation Examples 1 to 4), and the resulting solutions were cast to a thickness of 1~3 mm. The cast gels were irradiated with Co-60 gamma ray in radiation doses of 25, 35, 50 and 75 kGy, respectively, to crosslink the polymer chains to afford sterile hydrogels.

Example 8

Preparation of Polyacrylic Acid Hydrogel 2

The same procedure as in Example 7 was repeated, with the exception that an electron beam accelerator was used to afford hydrogels instead of the gamma ray source.

Example 9

Preparation of Polyacrylic Acid Hydrogel 3

Hydrogels were prepared in the same manner as in Example 4, with the exception that a photoinitiator was added to the solution and a UV lamp (230~400 nm) was used instead of the gamma ray source.

Example 10

Preparation of Water-Evaporation Preventive Film-Supported Hydrogel 1

6.5 wt % of polyvinylpyrrolidone, 2.5 wt % of carrageenan and 2 wt % of glycerin were mixed with 89 wt % of the extract prepared in one of Preparation Examples 14 and heated at 80° C. to yield a solution. This solution was cast to a thickness of 2 mm on a laminate of a hydrophilic non-woven fabric sheet and an air-permeable polyethylene film. After being cooled to room temperature, the gel supported by the laminate functioning as a water-evaporation preventive layer was packaged and irradiated with 25 key of radiation at a rate of 1 kGy/h to produce a hydrogel.

Example 11

Preparation of Water Evaporation Preventive Film-Supported Hydrogel 2

20 wt % of polyvinyl alcohol and 5 wt % of glycerin were mixed with 75 wt % of the extract prepared in one of Preparation Examples 1~4, and the mixture was autoclaved at 120° C. for 40 min to yield an aqueous polymer solution. This solution was cast to a thickness of 2 mm on a laminate of hydrophilic non-woven fabric sheet and air-permeable polyethylene film. The cast was frozen at −76° C. for 3 min and then thawed at room temperature to form a physically crosslinked structure therein. The resulting gel, supported by the laminate functioning as a water-evaporation preventive film, was packaged and irradiated with 25 kGy of radiation at a rate of 1 kGy/h to produce a hydrogel.

Experimental Example 1

Therapeutic Effect of Hydrogel on Contact Dermatitis

In order to examine the therapeutic effect of the hydrogel of the present invention on contact dermatitis, the following experiments were conducted.

<1-1> Effect of Relieving Edema in Mouse Models

Figure 3:
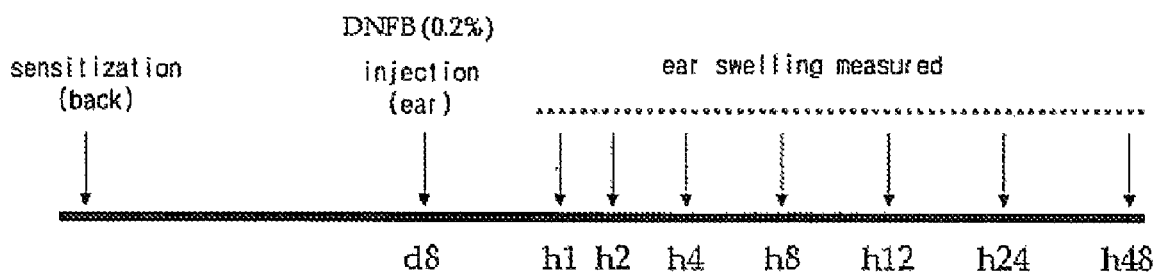
FIG. 3 shows experimental strategies in which 2,4-dinitrofluorobenzene(DNFB) is injected to cause contact dermatitis in non-treated mice (a) and hydrogel-pretreated mice (b), followed by measuring them for ear swelling over time (e.g., 1 hour after the injection (h1))
Figure 3:
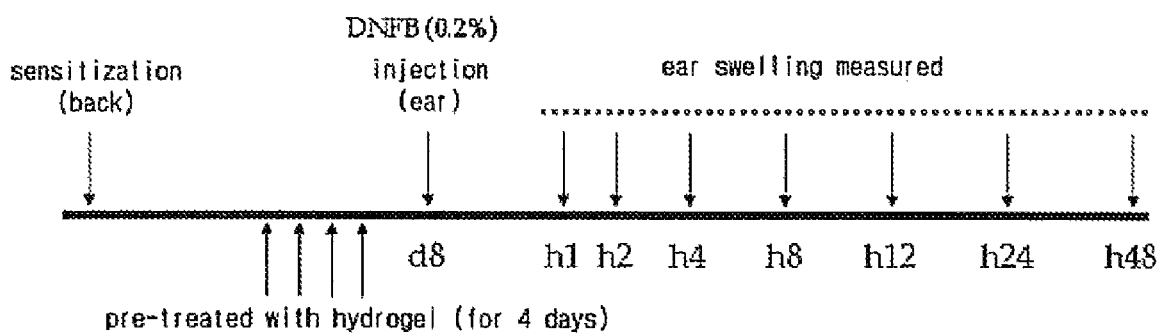

As shown in FIG. 3, C57BL/6 mice were shaved and a 0.5% dilution of DNFB(2,4-dinitrofluorobenzenz, St. Louis, Mo., USA) in a mixture of acetone:olive oil=4:1 was applied to the back of the mice to cause edema.

While a control was left untreated, mice in an experimental group were coated twice a day for 8 days with the hydrogel prepared in Examples 1~11. The mice were observed for dermatitis progression during that time. The results are shown in FIG. 4.

Figure 4:
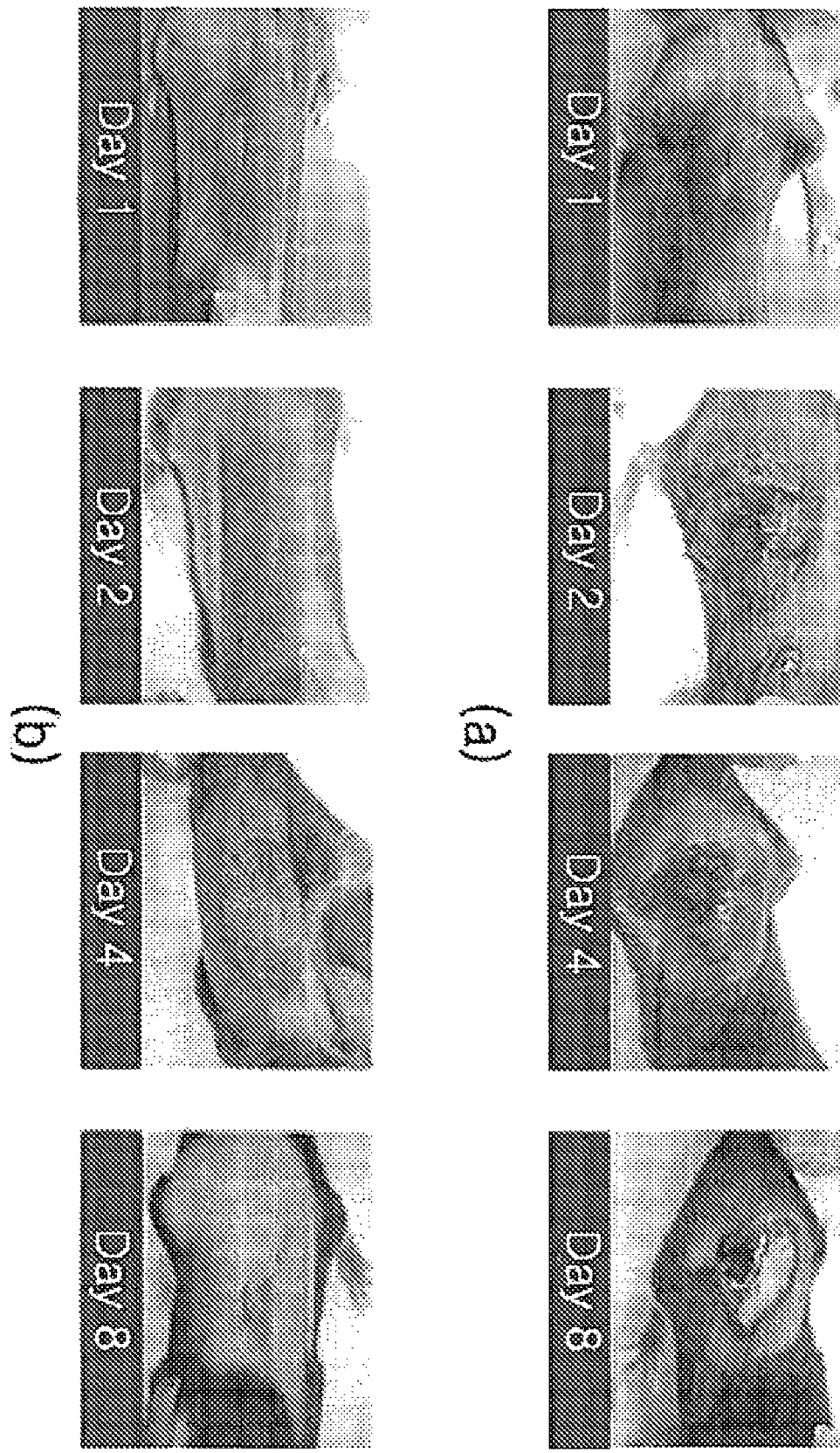
FIG. 4 provides photographs showing the progression of edema over time on the backs of mice which were treated without hydrogel (a) and with hydrogel (b)
Figure 5:
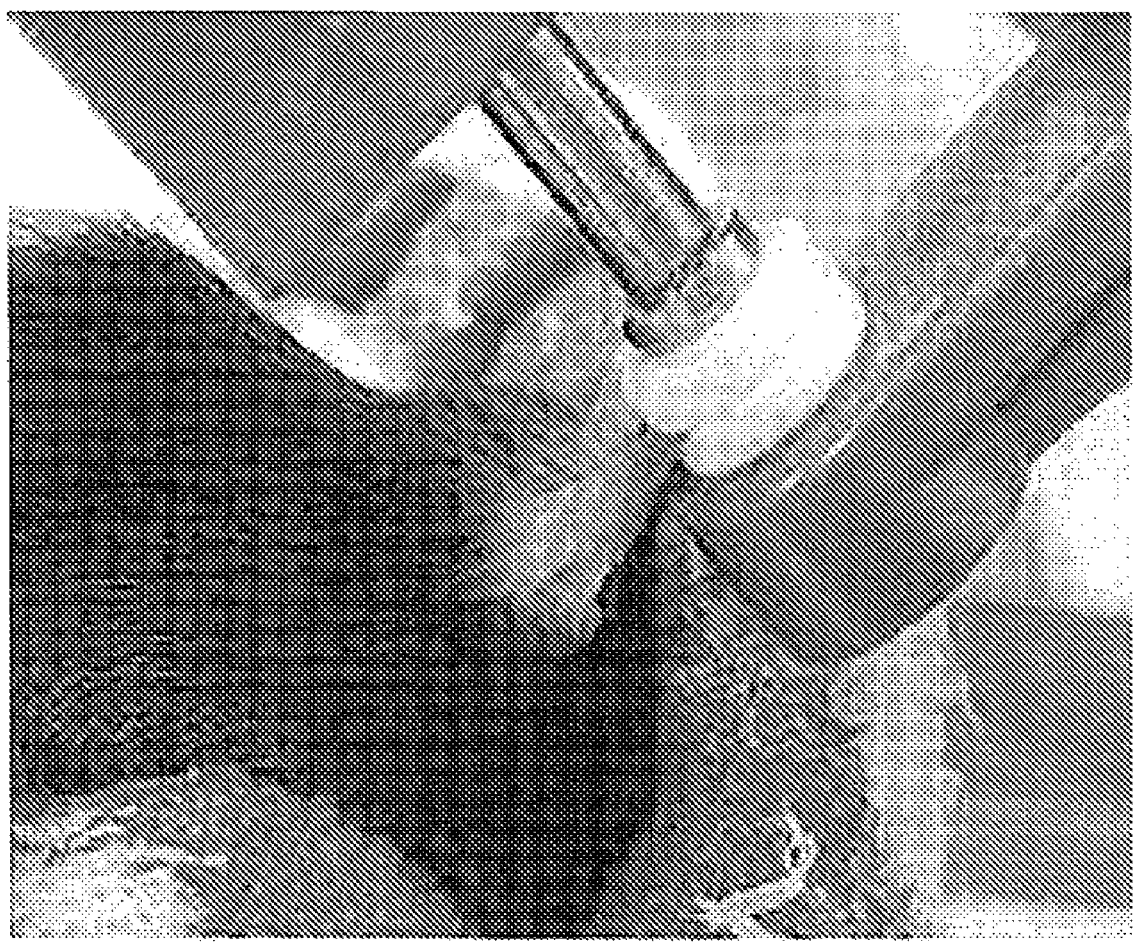
FIG. 5 is a photograph showing the measurement of ear swelling of a mouse suffering from contact dermatitis.

As is apparent from the photographs of FIG. 4, the mice coated with the hydrogel (b) gradually recovered from the edema whereas the control mice (a) suffered from increasingly deteriorated edema.

<1-2> Effect of Relieving Ear Edema in Mouse Models

Figure 6:
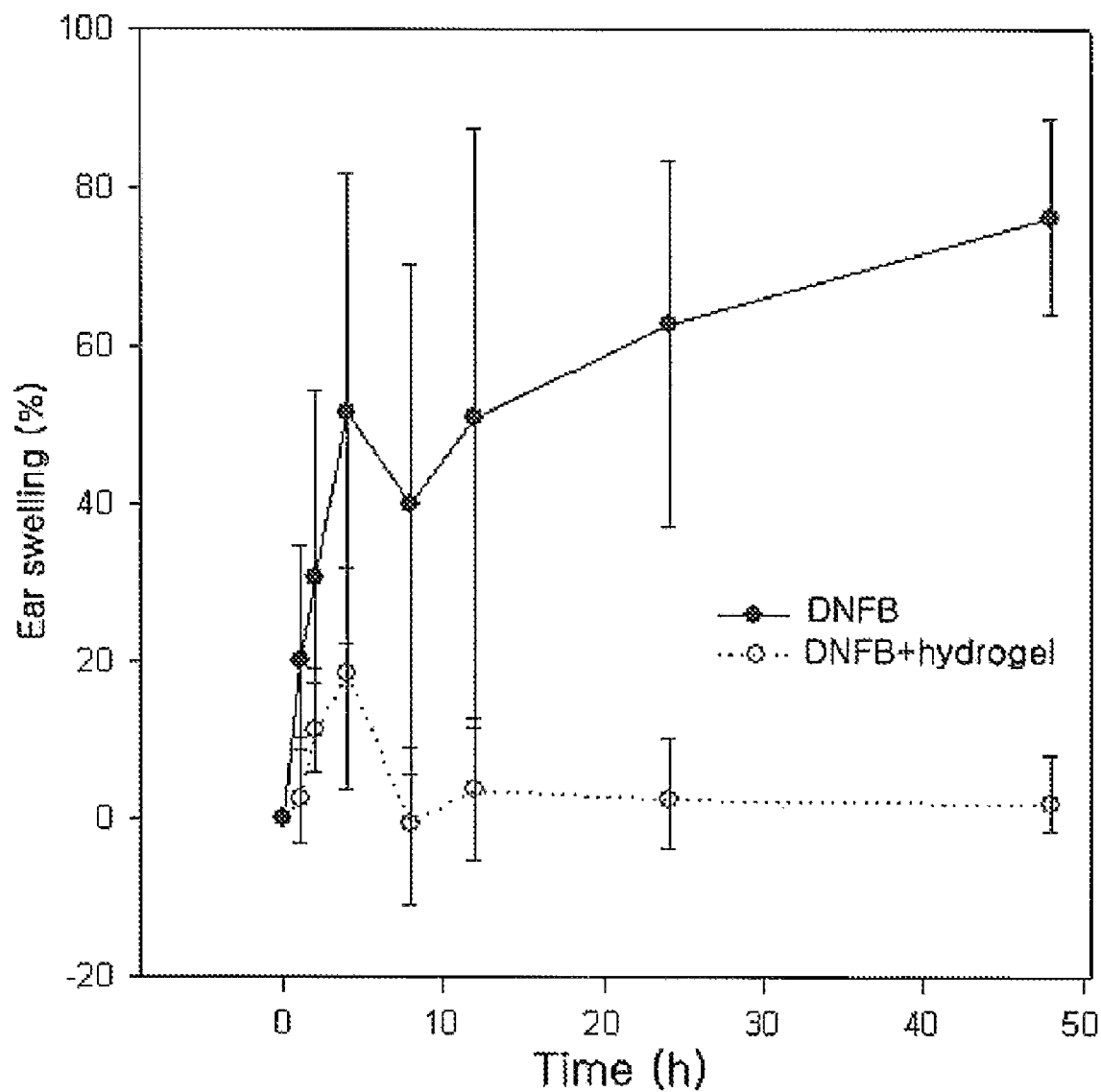
FIG. 6 is a graph showing the progression of ear swelling over time in the mice which are treated without hydrogel (-●-) and with hydrogel (•••○ •••) in advance of the injection of 2,4-dinitrofluorobenzene (DNFB) into the mice to induce contact dermatitis thereinto (n=200, p<0.001.)

After the experiment shown in FIG. 3, the hydrogel prepared in Examples 1~11 were applied twice a day for 4 days to the ear of the C57BL/6 mice while the control was not treated with the hydrogel. Afterwards, a 0.2% DNFB solution was applied to the ear of both the hydrogel-treated mice and the non-treated control to cause ear swelling. Using a micrometer (Mitutoyo Corp., Japan), as shown in FIG. 6, the mice were measured for changes in ear thickness over time. The results are given in FIG. 6.

As seen in the graph of FIG. 6, ear swelling was found to increase by 70% in the control, which was not treated with hydrogel in advance. In contrast, the ear swelling of the pre-treated mice increased by 20% in an early stage, but decreased to zero % over time.

Consequently, the hydrogel according to the present invention relieves contact dermatitis and can be effectively used as a therapeutic agent for dermatitis.

Experimental Example 2

Effect of Relieving Atopic Dermatitis in Mouse Model

In order to examine the therapeutic effect of the hydrogel of the present invention on atopic dermatitis, the following experiments were conducted.

The hydrogels prepared in Examples 1~11 were applied twice a day for 7 days to the dorsal neck of BALE/c mice. After 7 days of the pretreatment, an oligomeric mixture of condensation products of N-methyl-p-methoxyphenethylamine and formaldehyde (Compound 48/80, St. Louis, Mo., USA), was injected in a dose of 50 μg per mouse into the dermis of the dorsal neck of the pre-treated mice and the non-treated control mice.

Figure 7:
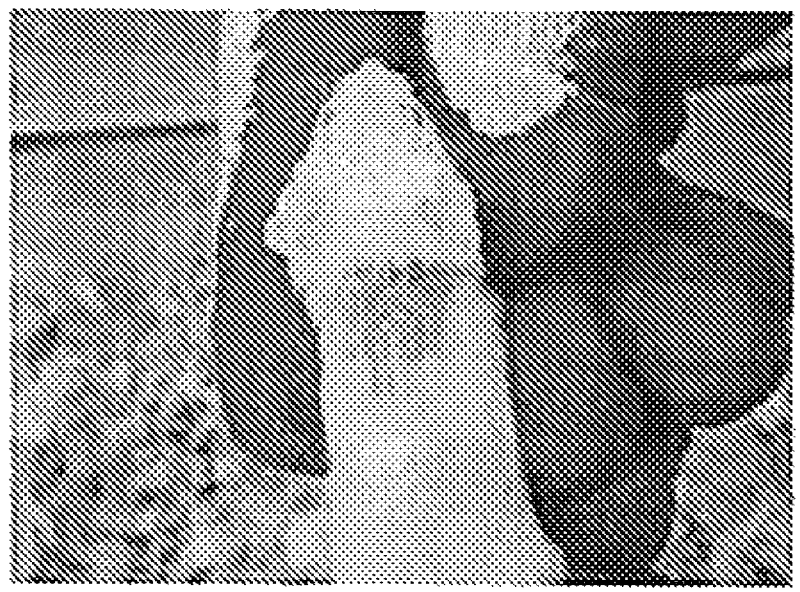
FIG. 7 is photographs showing the injection of compound 48/80 (an oligomeric mixture of condensation products of N-methyl-p-methoxyphenethylamine and formaldehyde) to mice to introduce atopic dermatitis therein.
Figure 7:
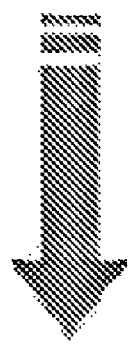
Figure 7:

The skin was found to break out in a rash accounting for atopic dermatitis, as seen in FIG. 7. Both the experimental mice and the control mice were caged and photographed for 60 min with a video camera to monitor the behaviors thereof.

The skin itchiness was assessed according to the method suggested by the Orito group. The mice were observed for scratching behavior and the number of scratches was counted over time. The results are graphed in FIG. 8.

Figure 8:
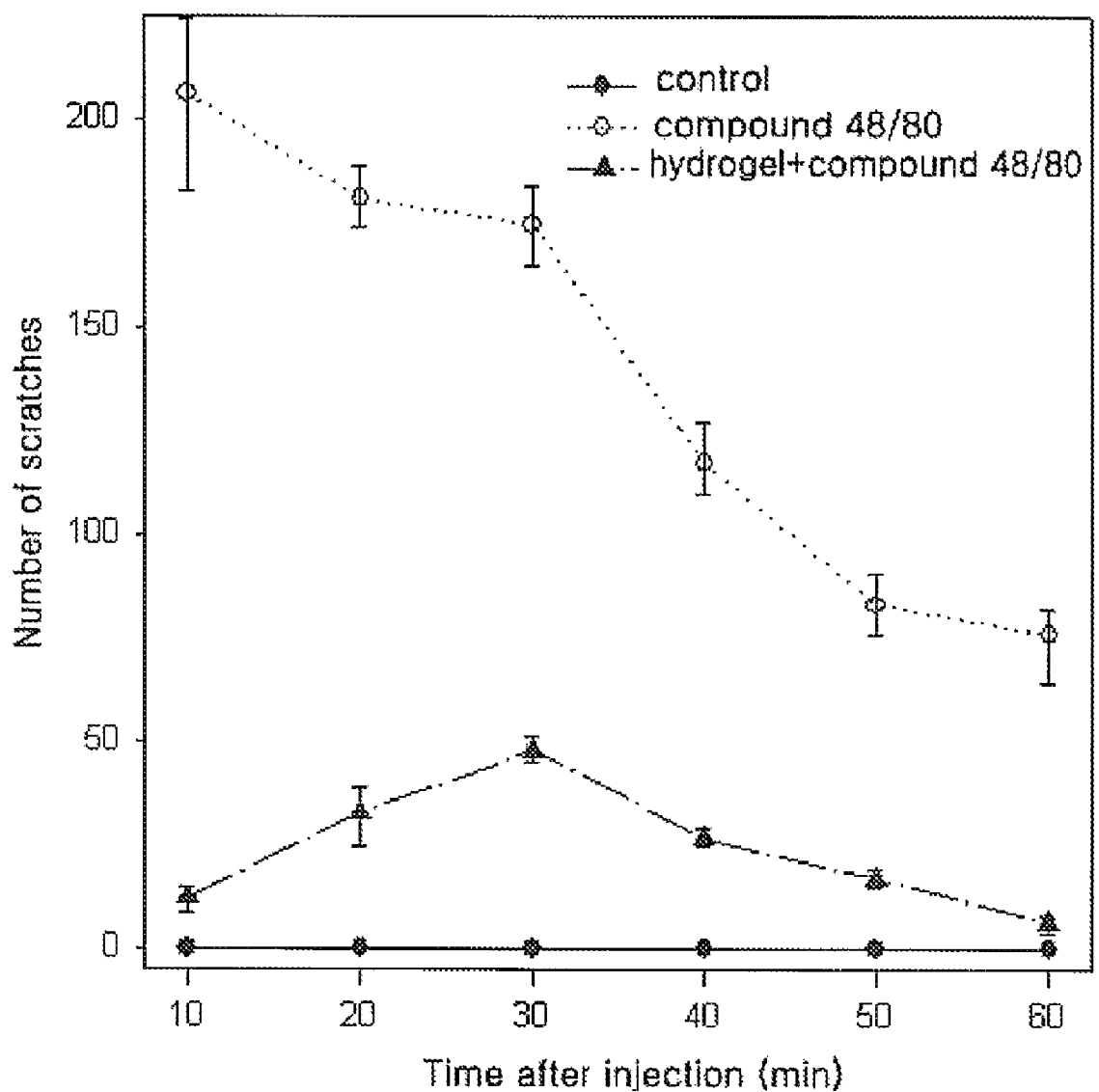
FIG. 8 is a graph showing the numbers of scratches over time in mice which were normal (-●-) and mice which were treated without hydrogel (•••○ •••) and with hydrogel (••▲-) in advance of the injection of compound 48/80 (an oligomeric mixture of condensation products of N-methyl-p-methoxyphenethylamine and formaldehyde) to introduce atopic dermatitis thereinto (n=100, p<0.001.)

As shown in FIG. 8, the control mice, into which dermatitis was introduced without pretreatment with the hydrogels prepared in Examples 1~2, were observed to scratch their necks about 100 times for the first 30 min. The number of scratches, although decreasing over time, amounted to 40 even 60 min after the rash broke out. In contrast, the mice into which atopic dermatitis was introduced after pretreatment were found to scratch the neck up to 40 times, and the number of scratches decreased over time, and approximated zero 60 min after the rash broke out.

Therefore, the hydrogel according to the present invention is proven to relieve the itchiness attributable to atopic dermatitis and thus can be effectively used for the treatment and prevention of atopic dermatitis.

Experimental Example 3

Experiment for Drying Hydrogel

In order to examine the effect of the laminate on the water evaporation of the hydrogel, the following experiment was performed.

Figure 9:
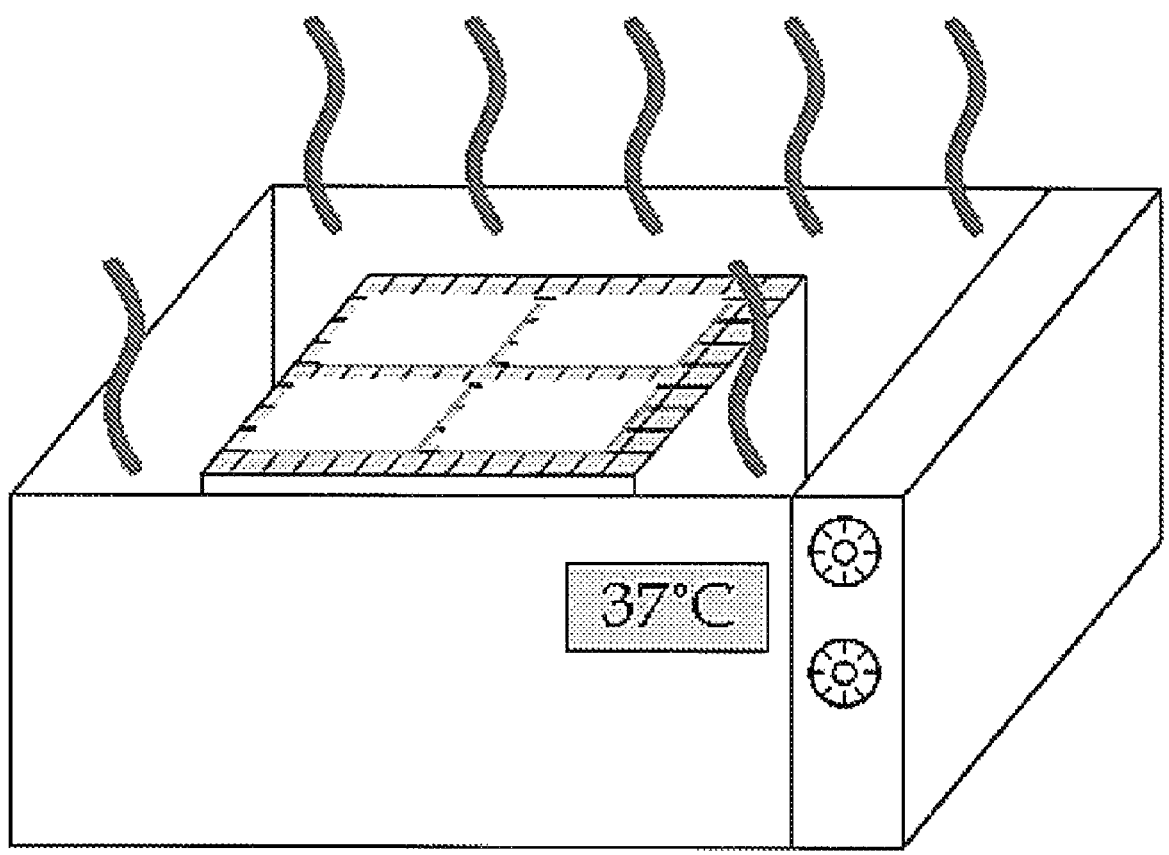
FIG. 9 is a schematic view showing a drying apparatus for measuring hydrogels for water evaporation over time.

The hydrogel, prepared in Example 1, which was not supported by a laminate, and the hydrogel, prepared in Example 16, which was supported by a laminate, were measured for water evaporation over time using a drying apparatus shown in FIG. 9. In the drier, water was maintained at 37° C., and the inner humidity was maintained at 60~80%. The hydrogels placed on the net of the drier were exposed to steam on the lower sides thereof and to air on the upper sides thereof.

The hydrogels were calculated for degree of water evaporation according to the following Mathematic Formula 1.

$$\text{Degree of Water Evaporation (\%)} = \frac{\text{Initial Gel Weight} - \text{Dried Gel Weight}}{\text{Initial Gel Weight}} \times 100 \quad \text{[Mathematic Formula 1]}$$

Figure 10:
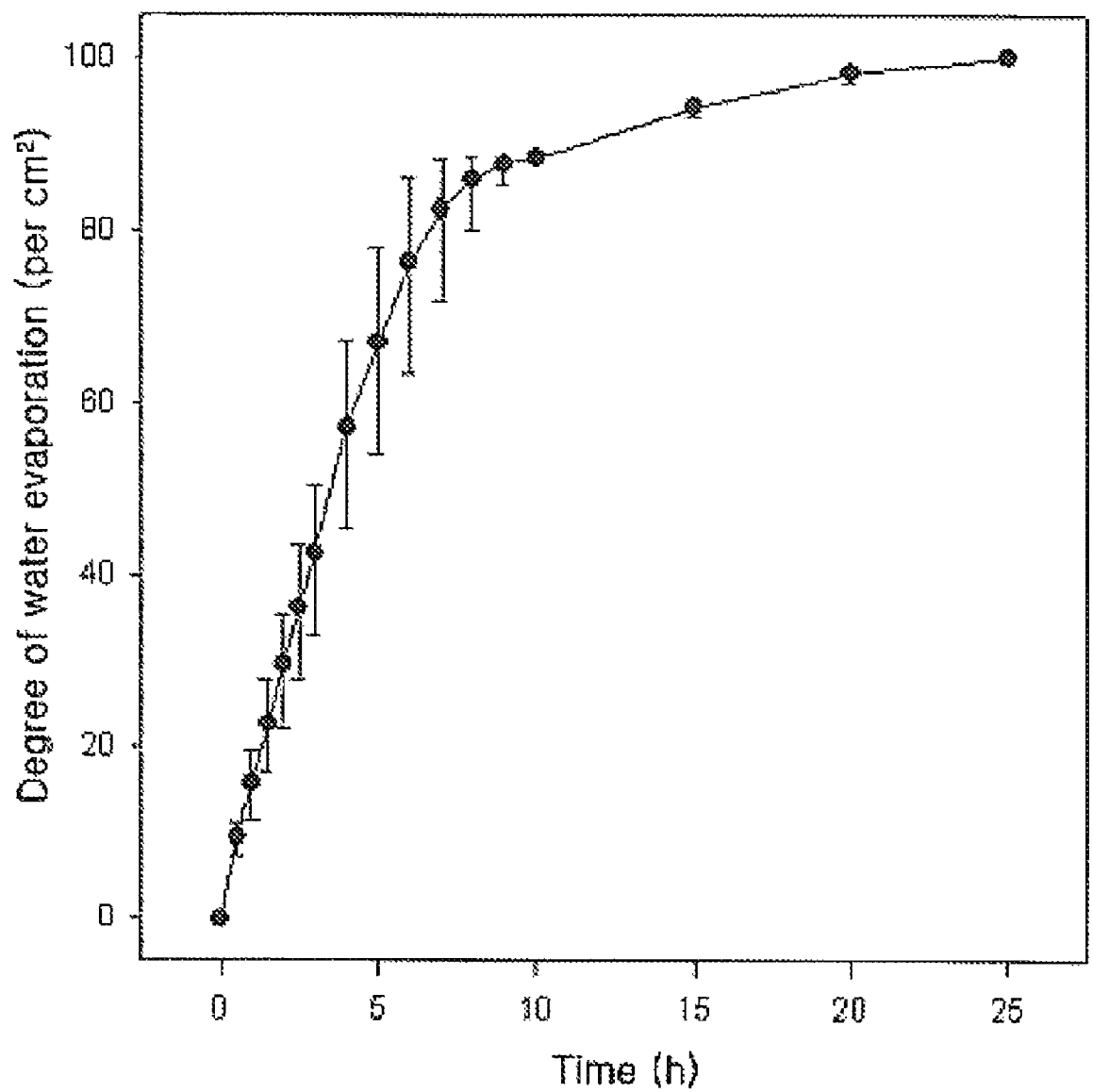
FIG. 10 is a graph showing the water evaporation over time of a hydrogel having no water evaporation preventive membranes.
Figure 11:
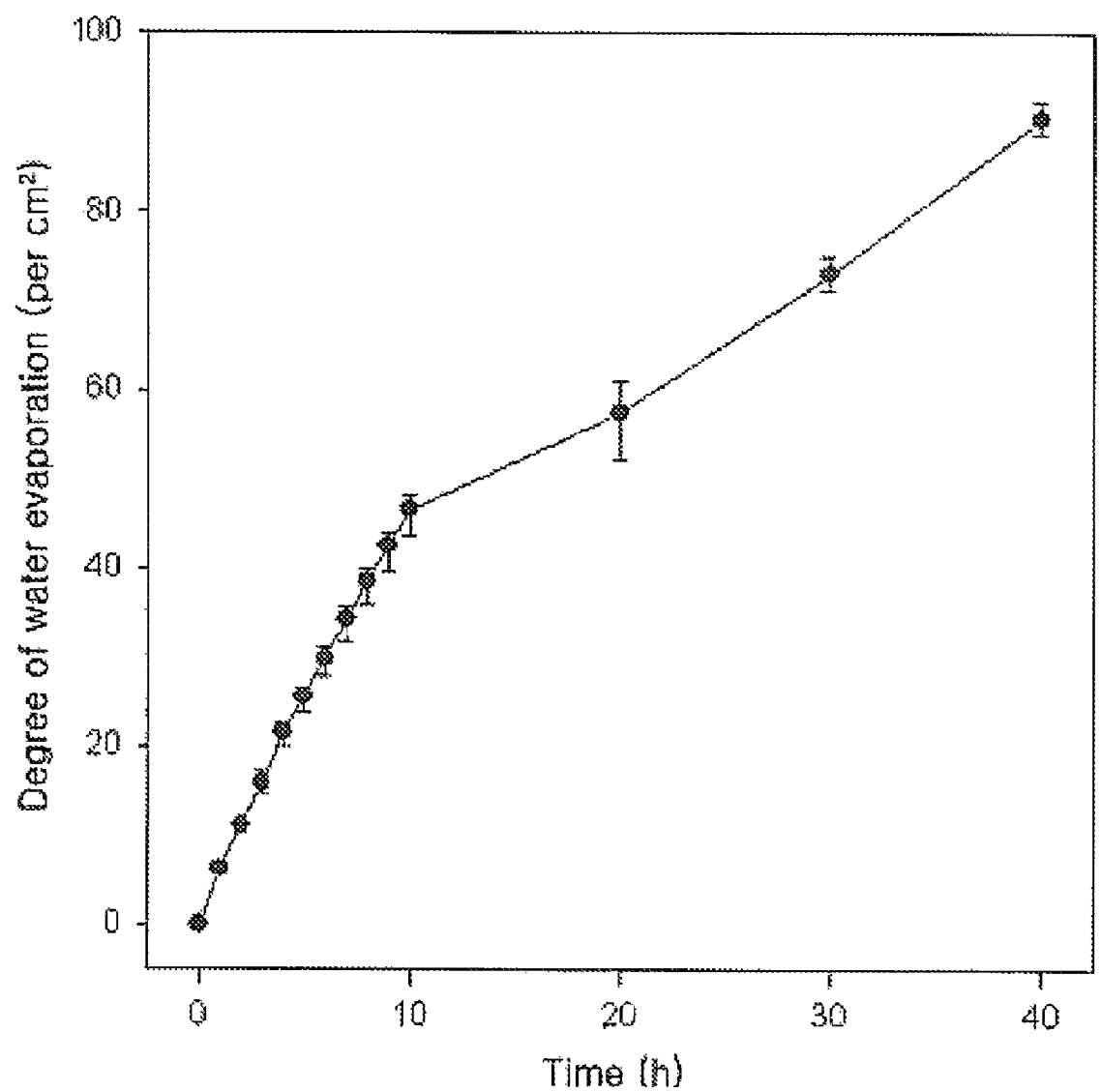
FIG. 11 is a graph showing the water evaporation over time of a hydrogel having a water evaporation preventive membrane.

Measurements of the degree of water evaporation are plotted in FIGS. 10 and 11.

FIG. 10 shows the degrees of water evaporation of the hydrogel, prepared in Example 1, which was not supported by the laminate, functioning as a preventive layer against water evaporation, while FIG. 11 shows the degrees of water evaporation of the hydrogel, prepared in Examples 10 and 11, which is supported by the laminate functioning as a preventive layer against water evaporation.

As can be understood from the data of FIGS. 10 and 11, the hydrogel, when not supported by the laminate, rapidly dried in the first 5 hours and was completely dehydrated within 20 hours, whereas the hydrogel supported by the laminate was found to retain water for more than 45 hours.

Able to remain wet for a long period of time, thus, the hydrogel comprising the water evaporation preventive layer is useful in the treatment of contact dermatitis or atopic dermatitis.

Experimental Example 4

Clinical Application of Hydrogel for Treatment of Atopic Dermatitis

In order to examine the effect of the hydrogel according to the present invention on atopic dermatitis, a clinical test was conducted as follows.

Figure 12:
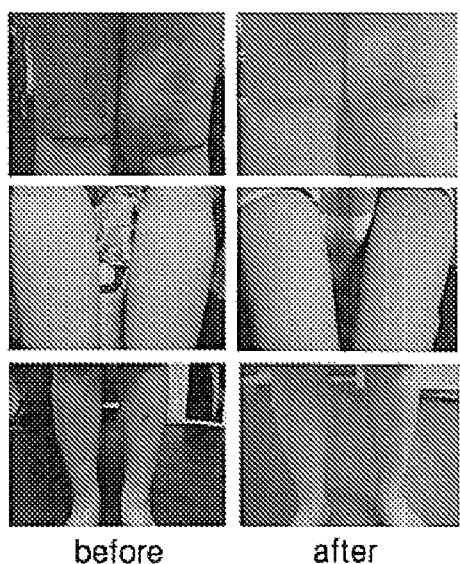
FIG. 12 provides photographs showing clinical effects of the hydrogel according to an embodiment of the present invention on dermatitis.
Figure 12:
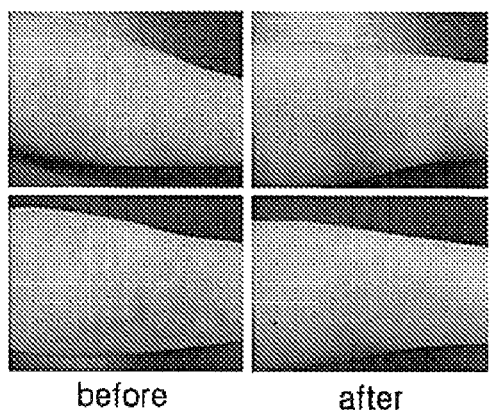
Figure 12:
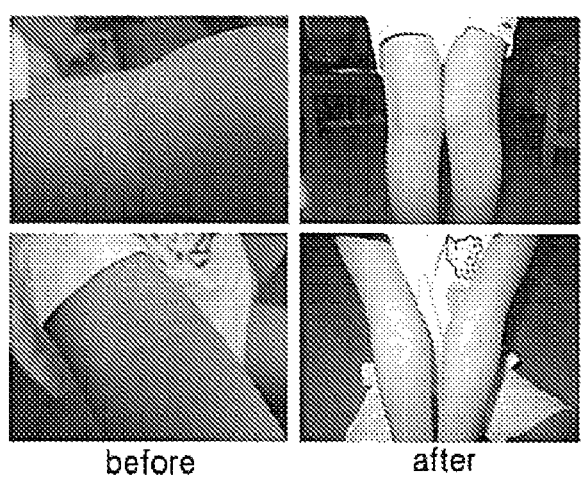
Figure 12:
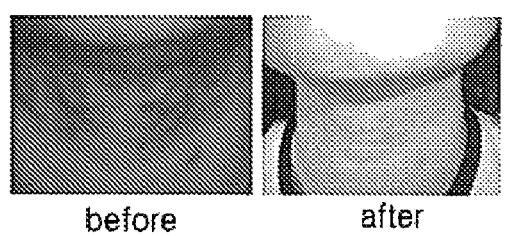

The hydrogels prepared in Examples 1 or 4 were applied twice a day for 7 days to patients with atopic dermatitis or another form of allergic dermatitis. The sites treated with the hydrogels were photographed every day to monitor the therapeutic effect of the hydrogels. The results are given in FIG. 12. As seen in FIG. 12, the hydrogels according to the present invention are demonstrated to prevent the inflammatory progression of atopic dermatitis or other dermatitis and to be useful in the treatment of atopic dermatitis.

As described hereinbefore, the hydrogels according to the present invention can carry medicinally effective ingredients for a sustained period of time and absorb wound exudates properly. The hydrogels have suitable gel strength and, when applied to a wound, can prevent bacterial infection of the wound. In addition, the radiation method according to the present invention allows the polymer chains to be crosslinked to each other, but also brings about a sterilization effect in the final hydrogel. There are no problems of toxic residues in the hydrogels. They are easy to attach to the skin and concomitantly provide a cool feeling. Supported by the laminate of hydrophilic non-woven fabric sheet and polyethylene film, the hydrogel retain water for a prolonged period of time and thus are useful in the treatment of contact dermatitis and atopic dermatitis.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A hydrogel for the treatment of atopic dermatitis, comprising
   1-50% by weight of a biocompatible polymer,
   1-20% by weight of a polyalcohol, and
   1-30% by weight of a medicinal plant extract obtained from a plant mixture of 5-25% by weight of *Houttuynia cordata,* 5-25% by weight of elm, 5-25% by weight of persimmon leaves, 5-25% by weight of celandine, 5-25% by weight of pine tree leaves, 5-10% by weight of *Canavalia gladiata* and 5-30% by weight of an herb selected from the group consisting of rosemary, lavender, spearmint, chamomile, rooibos and combinations thereof,
   wherein
   the hydrogel is prepared by irradiation to achieve crosslinking and sterilization of the hydrogel,
   the hydrogel contains a three-dimensional network structure formed by crosslinking; and
   the hydrogel is insoluble in water.

2. The hydrogel according to claim 1, wherein the biocompatible polymer is selected from the group consisting of polyvinyl alcohol, polyvinylpyrrolidone, polyacrylic acid, polyethylene oxide, carrageenan, sodium carboxymethyl cellulose, gelatin, agar, alginate, chitosan, and combinations thereof.

3. The hydrogel according to claim 1, wherein the polyalcohol is selected from the group consisting of glycerin, ethylene glycol, propylene glycol, 1,3-butylene glycol, hexylene glycol, sorbitol, mannitol, polyethylene glycol and combinations thereof.

4. The hydrogel according to claim 1, wherein the hydrogel is supported by a water evaporation preventive membrane.

5. The hydrogel according to claim 4, wherein the water evaporation preventive membrane is a laminate of a hydrophilic non-woven fabric sheet and an air-permeable polyethylene film.

6. The hydrogel according to claim 1, wherein the biocompatible polymer is polyvinyl alcohol.

7. The hydrogel according to claim 6, wherein the polyvinyl alcohol is in an amount of 20% by weight based on the total weight of the hydrogel.

8. The hydrogel according to claim 1, wherein the biocompatible polymer is a mixture of polyvinylpyrrolidone and carrageenan.

9. The hydrogel according to claim 8, wherein the polyvinylpyrrolidone is in an amount of 1-30% by weight and the carrageenan is in an amount of 1-5% by weight based on the total weight of the hydrogel.

10. The hydrogel according to claim 8, wherein the polyvinylpyrrolidone is in an amount of 7% by weight and the carrageenan is in an amount of 3% by weight based on the total weight of the hydrogel.

11. The hydrogel according to claim 1, wherein the biocompatible polymer is a mixture of polyacrylic acid and carrageenan.

12. The hydrogel according to claim 11, wherein the polyacrylic acid is in an amount of 1-20% by weight and the carrageenan is in an amount of 1-5% by weight based on the total weight of the hydrogel.

13. The hydrogel according to claim 11, wherein the polyacrylic acid is in an amount of 10% by weight and the carrageenan is in an amount of 3% by weight based on the total weight of the hydrogel.

14. The hydrogel according to claim 1, wherein the polyalcohol is glycerin.

15. The hydrogel according to claim 14, wherein the glycerin is in an amount of 5% by weight based on the total weight of the hydrogel.

16. The hydrogel according to claim 1, wherein the hydrogel has a thickness of 1-5 mm.

17. A hydrogel for the treatment of atopic dermatitis consisting essentially of
   1-50% by weight of a biocompatible polymer,
   1-20% by weight of a polyalcohol, and
   1-30% by weight of a medicinal plant extract obtained from a plant mixture of 5-25% by weight of *Houttuynia cordata,* 5-25% by weight of elm, 5-25% by weight of persimmon leaves, 5-25% by weight of celandine, 5-25% by weight of pine tree leaves, 5-10% by weight of *Canavalia gladiata* and 5-30% by weight of an herb selected from the group consisting of rosemary, lavender, spearmint, chamomile, rooibos and combinations thereof,
   wherein
   the hydrogel is prepared by irradiation to achieve crosslinking and sterilization of the hydrogel,
   the hydrogel contains a three-dimensional network structure formed by crosslinking; and
   the hydrogel is insoluble in water.

* * * * *